United States Patent [19]

Fröhlen

[11] Patent Number: 4,762,938

[45] Date of Patent: Aug. 9, 1988

[54] PROCESS FOR THE PREPARATION OF ALKOXYSILANES

[75] Inventor: Hans G. Fröhlen, Leverkusen, Fed. Rep. of Germany

[73] Assignee: Bayer Aktiengesellschaft, Leverkusen, Fed. Rep. of Germany

[21] Appl. No.: 103,120

[22] Filed: Sep. 28, 1987

[30] Foreign Application Priority Data

Oct. 10, 1986 [DE] Fed. Rep. of Germany ....... 3634524

[51] Int. Cl.[4] ............................ C07F 7/04; C07F 7/18

[52] U.S. Cl. .................................................... 556/470

[58] Field of Search ......................................... 556/470

[56] References Cited

U.S. PATENT DOCUMENTS 2,727,054 12/1955 Wright ............................... 556/470

4,226,793 10/1980 Kotzsch et al. ..................... 556/470

*Primary Examiner*—Paul F. Shaver

*Attorney, Agent, or Firm*—Connolly and Hutz

[57] ABSTRACT

Alkoxysilanes are prepared by reacting halosilanes with monohydric alcohols and a trialkyl phosphite.

8 Claims, No Drawings

PROCESS FOR THE PREPARATION OF ALKOXYSILANES

The present invention relates to an improved process for the preparation of monomeric alkoxysilanes by reacting chlorosilanes with alcohols in the presence of trialkyl phosphites.

BACKGROUND OF THE INVENTION

It has already been disclosed the the preparation of alkoxysilanes by reacting chlorosilanes with alcohols can be carried out both in the gas phase and in the liquid phase. Gas-phase reactions are described, for example, in DE-A No. 3,236,628 (=U.S. Pat. No. 4,506,087), DE-A No. 2,061,189 (=U.S. Pat. No. 3,792,071) and DE-A No. 3,000,782 (=U.S. Pat. No. 4,298,753). Reactions in the liquid phase, for example the reaction of chlorosilanes with alcohols in a stirred vessel, are described by British Patent Specification No. 674,137. Processes are likewise known in which the hydrogen chloride produced is expelled by means of inert gases (DE-B No. 862,895).

All these processes thus differ from one another in how the hydrogen chloride produced during the esterification is removed. It is absolutely necessary to remove the hydrogen chloride from the reaction mixture quickly in order to ensure complete reaction, to obtain a product which is free of hydrogen chloride, and to prevent undesired side reactions, such as, for example, the formation of polysiloxanes. In order to achieve this, expensive and complicated plants are necessary which, because of the hydrogen chloride produced, must in addition be manufactured from expansive materials. In addition, the removal of the final traces of —Si—Cl groups is difficult.

The method described by A. Gancberg and J. Vandevelde in Industrie Chemique Belge No. 6,591 (1964) for obtaining alkoxysilanes by converting alkyl orthoformates can hardly be achieved industrially if only for cost reasons. In addition, large amounts of alkyl formates are produced during this reaction.

BRIEF DESCRIPTION OF THE INVENTION

The object was therefore to find a process which permits the preparation of monomeric alkoxysilanes without the disadvantages of the processes known hitherto. The present invention achieves this industrial object in such a fashion by the esterification of chlorosilanes using alcohols by adding stoichiometric amounts of trialkyl phosphites. Those phosphites are easily accessible industrially and represent products which are prepared on a large scale. It is an advantage of the inventive process that only utilizable products are obtained (i.e., alkoxysilanes, dialkyl phosphites and alkyl chlorides). When trimethyl phosphite is used, for example, dimethyl phosphite (useful as a starting material for insecticides and phosphonocarboxylic acids) and methyl chloride (useful in the Rochow synthesis of methyl chlorosilanes) are obtained in addition to the desired methoxysilane.

DETAILED DESCRIPTION

The invention thus relates to a process for the preparation of alkoxysilanes of the formula

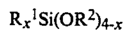

$$R_x{}^1Si(OR^2)_{4-x}$$

in which $R^1$, independently of one another, represents hydrogen or an optionally substituted $C_1$–$C_4$ alkyl or alkenyl radical, or an optionally substituted aryl radical having up to 10 C atoms, $R^2$ represents an alkyl radical having up to 4 C atoms, and X adopts the value 0, 1, 2 or 3, which is characterized in that halogenosilanes, in particular chlorosilanes, are reacted with monohydric alcohols and trialkyl phosphites.

The chlorosilanes to be employed as starting materials according to the process claimed correspond to the formula:

$$R_x{}^1SiCl_{4-x}$$

in which x can have the value 3, 2, 1 or 0, and $R^1$, independently of one another, can represent hydrogen or an optionally substituted $C_1$–$C_4$ alkyl or alkenyl radical, an optionally substituted alkyl radical or, alternatively, simultaneously different abovementioned radicals. In place of chlorosilanes, bromosilanes or iodosilanes may alternatively be employed.

The process according to the invention can be represented by the following equation:

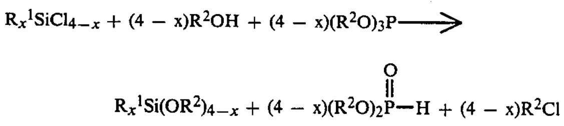

$$R_x{}^1SiCl_{4-x} + (4-x)R^2OH + (4-x)(R^2O)_3P \longrightarrow R_x{}^1Si(OR^2)_{4-x} + (4-x)(R^2O)_2\overset{O}{\overset{\|}{P}}-H + (4-x)R^2Cl$$

The following chlorosilanes are examples by starting materials: silicon tetrachloride, trichlorosilane, dimethyldichlorosilane, trimethylchlorosilane, vinyltrichlorosilane, 1-chloromethyltrichlorosilane, isobutyltrichlorosilane, 2-cyanoethyltrichlorosilane, phenyltrichlorosilane, diphenyldichlorosilane, methylphenyldichlorosilane, methylvinyldichlorosilane, methyltrichlorosilane, ethyltrichlorosilane and 3-chloropropyltrichlorosilane.

It is also possible to employ mixtures of different chlorosilanes.

The trialkyl phosphites $(R^2O)_3P$ used in the invention can be, for example: trimethyl phosphite, triethyl phosphite, triisopropyl phosphite or tris-(2-ethylhexyl)-phosphite, with the low-boiling and industrially easily accessible methyl and ethyl derivatives being preferred. The industrial suitability of the alkyl halides is also a criterion for selection. In order to avoid ligand exchange, it is expedient for the radicals $R^2$ in the alchols and $R^2$ in the trialkyl phosphites to be identical. Thus the alcohols used in the present invention have the formula $R^2$—OH. Examples of suitable alcohols include methanol, ethanol, n-propanol, isopropanol, n-butanol, isobutanol and tert.-butanol.

The process according to the invention can be carried out, for example, by initially mixing the trialkyl phosphite and the appropriate alcohol, and then adding the chlorosilane. However, it is also possible to initially mix the trialkyl phosphite and the chlorosilane, and then add the appropriate alcohol. This route also leads to the desired result. In addition to a batchwise preparation procedure, it is furthermore possible to prepare the desired alkoxysilanes in a continuous fashion. In this case, the starting compounds are metered separately into the first reactor of a multistage, for example two-stage, reaction cascade.

The amounts of the starting components are preferably selected so that about 1 mole of trialkyl phosphite and about 1 mole of alcohol are present for each gram-atom of Si-bound halogen.

If the radicals $R^2$ are, for example, $CH_3$ or $C_2H_5$, some of the alkyl halide $R^2Cl$ produced escapes in gaseous form during the reaction. Those skilled in the art know how the alkyl chloride can be recovered in such cases.

The usually exothermic reaction should be carried out at temperatures between about −20° C. and +80° C., a range from 40° to 70° C. being preferred for practical reasons. This does not mean that the reaction cannot likewise be controlled at even lower or even higher temperatures. In general, the reaction proceeds very quickly in the preferred temperature range. In the case of batchwise preparations, the reaction duration is limited, for example, only by the rate of heat dissipation and by control of the amount of alkyl chloride escaping. Subsequent heating in order to complete reactions is not necessary. In continuous reaction control, the same criteria apply, i.e., the physical parameters of materials supply and removal, heat dissipation, and so forth are limiting.

The reacted crude mixture is worked up by distillation. Depending on the type of reflux condenser, a more or less large part of the low-boiling alkyl halides escape in relatively pure form as early as during the reaction, and can be collected, for example, in cold traps.

In addition, the distillative separation is carried out in a fashion known to those skilled in the art with the aid of batchwise or continuous distillation through columns of sufficient column efficiency. In this separation, it may be expedient to distil the dialkyl phosphites, which are usually produced as high-boiling substances, under reduced pressure.

If the difference between the boiling points of the starting material trialkyl phosphite and the alkoxysilane produced is only slight (example methyltrimethoxysilane: boiling point 103° C., trimethyl phosphite: boiling point 108° C.), traces of the strongly smelling trialkyl phosphites which are present due to metering errors can be eliminated by special measures. For this purpose, the addition of sulphur (boiling point of $(CH_3O)_3PS$ = 186° C.) and the Arbuzov rearrangement (boiling point of $CH_3P(O)(COCH_3)_2$ = 175° C.) are particularly suitable. Simple distillative separation is subsequently possible.

The alkoxysilanes prepared according to the invention are suitable, for example, as crosslinking agents in cold-curing silicone materials, as starting materials for the preparation of coating materials (for example for scratchproofing), for silicone resins and for water-dispersible silicas.

The process according to the invention is illustrated in greater detail with reference to the following examples.

EXAMPLE 1

System: $(CH_3)_3SiCl/(CH_3O)_3P + CH_3OH$ 55 g (0.5 mol) of trimethylchlorosilane and 62 g (0.5 mol) of trimethyl phosphite are placed in a 250 ml three-neck flask equipped with stirrer, thermometer, dropping funnel, reflux condenser and a downstream dry-ice cold trap. 16 g (0.5 mol) of methanol are added within 10 minutes with stirring. The reaction temperature is kept at about 20° C. by external water cooling. When the addition of the methanol is complete, the reaction mixture is heated to boiling in order to expel the partially dissolved methyl chloride. A temperature of about 65° C. is produced in the reaction mixture during this heating.

The amount of methyl chloride collected in the cold trap is 24.5 g (=97% of theory).

The weight of the crude product mixture is 103 g. The gas chromatogram produced from this mixture contains the following major components:

48.7% of trimethylmethoxysilane (=96.4% of theory)

47.5% of dimethyl phosphite (=89% of theory).

EXAMPLE 2

System: $(CH_3O)_3P/CH_3OH + (CH_3)_3SiCl$ 62 g (0.5 mol) of trimethyl phosphite and 16 g (0.5 mol) of methanol are placed in an apparatus corresponding to Example 1 and heated to boiling. The temperature produced in the mixture in the apparatus is 67° C. During the addition (15 minutes) of 55 g (0.5 mol) of trimethylchlorosilane, the temperature in the reaction mixture falls to 46° C.

After work-up by distillation, the following yields are obtained:

24 g of methyl chloride (=95.1% of theory)

48 g of trimethylmethoxysilane (=92.3% of theory)

52 g of dimethyl phosphite (=94.5% of theory)

2.4 g of a higher-boiling residue.

EXAMPLE 3

System: $(C_2H_5O)_3P/C_2H_5OH + (CH_3)_2SiCl_2$ 166 g (1 mol) of triethyl phosphite and 46 g (1 mol) of ethanol are placed in an apparatus analogous to Example 1, but equipped with a 500 ml three-neck flask. Starting at room temperature, 65 g (0.5 mol) of dimethyl dichlorosilane are added within half an hour. The temperature increases rapidly and is checked at 50° C. by water cooling and kept at this level during the addition of the chlorosilane.

After evaluation by gas chromatography, the following result is obtained:

21.9% of ethyl chloride (=93.9% of theory)

24.0% of dimethyldiethoxysilane (=91.5% of theory)

47.9% of dimethyl phosphite (=96% of theory).

EXAMPLE 4

System: $(CH_3O)_3P/CH_3OH + SiCl_4$

The reaction between silicon tetrachloride and methanol in the presence of trimethyl phosphite is described.

For this reaction, 124 g (1 mol) of triethyl phosphite and 32 g (1 mol) of methanol are placed in an apparatus corresponding to Example 1. 42.5 g (0.25 mol) of silicon tetrachloride are added within 10 minutes. The heat of reaction is dissipated by means of a water bath so that a reaction temperature of 40° C. is produced. When the addition is complete, the mixture is heated, and the major part of the methyl chloride is thus expelled. A reflux temperature of 120° C. is produced.

Weight of methyl chloride (cold trap):

48.5 g (=96% of theory).

The gas-chromatographic analysis of the crude product mixture has the following composition:

23.6% of tetramethoxysilane (=91.4% of theory)

73.1% of dimethyl phosphite (=98.4% of theory)

EXAMPLE 5

System: $(CH_3O)_3P/CH_3OH+CH_2=CH-SiCl_3$

For the preparation of vinyltrimethoxysilane, use is made of a reactor as described in Example 1, but provided with a three-neck flask of capacity of 1 liter.

162 g (1 mol) of vinyltrichlorosilane are added within one hour to a mixture of 372 g (3 mol) of trimethyl phosphite and 96 g (3 mol) of methanol. The temperature in the reaction vessel is kept between 40° and 50° C. by water cooling. When the addition of chlorosilane is complete, the reaction mixture is heated to boiling, a temperature of about 110° C. being produced in the reaction mixture.

Evaluation of the crude product by gas chromatography gives the following major peaks:

29.4% of vinyltrimethoxysilane (=94.9% of theory)
67.6% of dimethyl phosphite (=97.9% of theory).

EXAMPLE 6

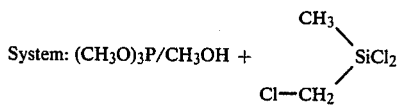

248 g (2 mol) of trimethyl phosphite and 64 g (2 mol) of methanol are placed in an apparatus analogous to Example 5. 164 g (1 mol) of methylchloromethyldichlorosilane are added within 30 minutes with stirring. The reaction temperature is kept at 50° C. by cooling. After work-up by distillation, the following amounts of product are obtained:

99.0 g of methyl chloride (≙98.0% of theory)
143.5 g of methylchloromethyldimethoxysilane (≙92.8% of theory)
201.0 g of dimethyl phosphite (≙91.3% of theory).

EXAMPLE 7

System: $(CH_3O)_3P/CH_3OH+(C_6H_5)_2SiCl_2$ 124 g (1 mol) of trimethyl phosphite and 32 g (1 mol) of methanol are placed in an apparatus analogous to Example 3, and 126.5 g (0.5 mol) of diphenyldichlorosilane are added within 20 minutes. The reaction temperature is controlled by water cooling so that 40° C. is not exceeded in the reaction mixture. When the exothermic phase has subsided, the reacted product is heated to 120° C. in order to expel the remaining, still dissolved methyl chloride.

Amount of methyl chloride collected:
46 g (≙90% of theory).

The weight of the crude product mixture is 467 g.

The gas chromatogram produced from this mixture has the following composition:

1.0% of methyl chloride (≙9.3% of theory)
47.0% of dimethyl phosphite (≙99.7% of theory)
48.9% of diphenyldimethoxysilane (≙93.6% of theory)

EXAMPLE 8

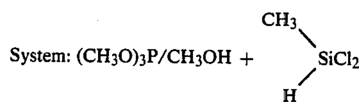

62 g (0.5 mol) of trimethyl phosphite and 16 g (0.5 mol) of methanol are placed in an apparatus analogous to Example 1. 29 g (0.25 mol) of methyldichlorosilane are added within 15 minutes at a temperature of 30° to 35° C. in the reaction mixture. The heat of reaction is dissipated by water cooling.

When the addition is complete, the reaction mixture is heated until reflux is produced.

Methyl chloride (cold-trap contents):
26 g (≙100% of theory).

Weight of remaining reaction mixture: 82 g.

Evaluation by gas chromatography has the following result:

29.5% of methyldimethoxysilane (≙90.7% of theory)
63.7% of dimethyl phosphite (≙94.4% of theory)

EXAMPLE 9

System: $(CH_3O)_3P/CH_3OH+(CH_3)_2SiCl_2$ 248 g (2.0 mol) of trimethyl phosphite and 64 g (2.0 mol) of methanol are placed in an apparatus analogous to Example 5, and 125 g (1.0 mol) of dimethyldichlorosilane are added within 30 minutes. The reaction temperature is kept at 50° C. by external cooling (water bath). The methyl chloride escaping via the condenser is condensed in a trap cooled with dry ice. In order to expel the remaining amounts of methyl chloride, the reaction mixture is heated until reflux occurs at 95° C. For separation, the dimethyl-dimethoxysilane/dimethyl phosphite mixture remaining is distilled, initially at atmospheric pressure, over a 1 m column (internal diameter 50 mm) charged with 6 mm porcelain saddles at a reflux ratio of 1:1. Under these conditions, 95% of the amount of dimethyldimethoxysilane to be expected are to obtained. In order to prevent overheating of the dimethyl phosphite remaining, the pressure is reduced to 15 mbar.

When the work-up is completed, 109 g (91.0% of theory) of dimethyldimethoxysilane having a purity of 99.9% and 212 g of dimethyl phosphite (96.4% of theory) having a purity of 99.8% are obtained.

EXAMPLE 10

System: $CH_3SiCl_3/(CH_3O)_3P/CH_3OH$, continuous 397 ml (504 g) of methyltrichlorosilane, 410 ml (324 g) of methanol and 1194 ml (1255 g) of trimethyl phosphite are metered, using metering pumps, per hour into the first reactor of a reaction cascade, consisting of glass with Teflon connections, with internal cooling coils of metal and a capacity of 0.5 liters per reactor, and brought to reaction with stirring. The reaction temperature in both stages is kept at 40° C. with the aid of the cooling coils. The average residence time in the plant is about 0.5 hours. The methyl chloride escaping via the condenser is collected in a trap cooled with dry ice. The discharge sample from reactor 2 has the following composition according to evaluation by gas chromatography:

22.9% of methyl chloride
26.3% of methyltrimethoxysilane
49.3% of dimethyl phosphite.

In order to determine the yield, exactly one hourly quantity is branched off from the product stream and worked up by distillation. From this, the following amounts of pure product are obtained:

Methyltrimethoxysilane 428.5 g (≙93.5% of theory)
Dimethyl phosphite 1,070.9 g (≙96.3% of theory)
Methyl chloride 504.4 g (≙98.8% of theory).

EXAMPLE 11

System: $CH_3(CH_2{=}CH)SiCl_2/(CH_3O)_3P/CH_3OH$, continuous

Methylvinyldimethoxysilane is likewise prepared in the reaction cascade analogous to the preparation of methyltrimethoxysilane. Throughput and reaction temperature are about the same as those for the preparation of methyltrimethoxysilane. Yields:

Methylvinyldimethoxysilane 90.6% of theory

Dimethyl phosphite 97.2% of theory

Methyl chloride 99.0% of theory.

What is claimed is:

1. In an improved process for the preparation of alkoxysilanes of the formula $$R_x^1Si(OR^2)_{4-x}$$

by reacting a halosilane with an alcohol wherein:

each $R^1$, independently of one another, represents hydrogen, $C_1$–$C_4$-alkyl, $C_2$–$C_4$-alkenyl, or aryl having 6 to 10 carbon atoms;

$R^2$ represents alkyl having 1 to 4 carbon atoms; and x has the value 0, 1, 2 or 3;

the improvement comprises reacting the halosilane with monohydric alcohol and a trialkyl phosphite.

2. The process according to claim 1 wherein the amount of reactants is about 1 mole of trialkyl phosphite and 1 mole of alcohol per gram-atom of Si-bound halogen.

3. The process according to claim 1 wherein the halosilane is a chlorosilane.

4. The process according to claim 1 wherein the halosilane is silicon tetrachloride, trichlorosilane, dimethyldichlorosilane, trimethylchlorosilane, vinyltrichlorosilane, 2-cyanoethyltrichlorosilane, phenyltrichlorosilane, diphenyldichlorosilane, methylphenyldichlorosilane, methylvinyldichlorosilane, methyltrichlorosilane, ethyltrichlorosilane, 3-chloropropyltrichlorosilane or mixtures thereof.

5. The process according to claim 1 wherein the trialkyl phosphite has the formula $(R^2O)_3P$ wherein $R^2$ is alkyl having 1 to 4 carbon atoms.

6. The process according to claim 1 wherein the trialkyl phosphite, triisopropyl phosphite or tris-(2-ethylhexyl)phosphite.

7. The process according to claim 1 wherein the trialkyl phosphite is trimethyl phosphite.

8. The process according to claim 1 wherein the trialkyl phosphite is triethyl phosphite.

* * * * *